United States Patent
Feitsma et al.

(10) Patent No.: US 11,751,523 B2
(45) Date of Patent: Sep. 12, 2023

(54) NON R-GENE MEDIATED RESISTANCE

(71) Applicant: RUK ZWAAN ZAADTEELT EN ZAADHANDEL B.V., De Lier (NL)

(72) Inventors: Johannes Geert Jan Feitsma, De Lier (NL); Vincent Laurens Adrianus Kock, De Lier (NL); Jan Hugo Den Braber, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 561 days.

(21) Appl. No.: 16/223,491

(22) Filed: Dec. 18, 2018

(65) Prior Publication Data

US 2019/0104700 A1 Apr. 11, 2019

Related U.S. Application Data

(63) Continuation of application No. 15/153,927, filed on May 13, 2016, now Pat. No. 10,226,016.

(51) Int. Cl.
- A01H 6/02 (2018.01)
- A01H 5/12 (2018.01)
- A01H 1/04 (2006.01)

(52) U.S. Cl.
CPC ............ *A01H 6/028* (2018.05); *A01H 1/04* (2013.01); *A01H 5/12* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2009/0300786 A1* 12/2009 Baerends .............. A01H 6/028
                                                    800/278
2013/0230635 A1    9/2013 Den Braber

FOREIGN PATENT DOCUMENTS

WO     2013/064436      5/2013
WO     WO2018/059651 A1 *  4/2018

OTHER PUBLICATIONS

Hallavant & Ruas (2014) Veget Hist Archaeobot 23:153-65.*
Irish et al. (2007) Plant Dis 91:1392-96.*
She et al. (2018) Theor Appl Genet 131:2529-41.*
Correll et al. (2011) Eur J Plant Pathol 129:193-205.*
Irish et al. (2008) Phytopath 90(8):894-900.*
As_Definition of as by Merriam-Webster_2017.
Feng et al., Plant Dis 98(1):145-52 (2014).
Reinmann-Philipp et al., Untersuchungen über die Kopplung von Resistenz-Faktoren beim Spinat in ihrer Bedeutung fur das Verständnis von dauerhafteren, weniger durch einen Zusammenbruch gefährdeten Resistenzen, Z. Pflanzenzchtg. (1975) 75:327-332.
Feng et al., Construction of a Spinach Bacterial Artificial Chromosome (BAC) Library as a Resource for Gene Identification and Marker Development, Plant Mol. Biol. Rep. (2015) 33:1996-2005.
Handke, et al., Detection of a Linkage of the Four Dominant Mildew Resistance Genes "M1M2M3M4" in Spinach from the Wildtype Spinacia Turkestanica, Gartenbauwissenschaft (2000) 65(2):73-78.

* cited by examiner

*Primary Examiner* — Russell T Boggs
(74) *Attorney, Agent, or Firm* — Duane Morris LLP; Thomas J. Kowalski; Deborah L. Lu

(57) ABSTRACT

The invention relates to plants and plant parts, in particular spinach plants (*Spinacia oleracea* L.), which are resistant to *Peronospora farinosa* f. sp. *spinaciae*. The invention also relates to seeds capable of producing *Peronospora farinosa* f. sp. *spinaciae* resistant plants. The invention further relates to methods for obtaining said plants with altered genotypes and seeds thereof, which are resistant to *Peronospora farinosa* f. sp. *spinaciae*.

19 Claims, No Drawings
Specification includes a Sequence Listing.

NON R-GENE MEDIATED RESISTANCE

RELATED APPLICATIONS AND INCORPORATION BY REFERENCE

This application is a continuation of U.S. application Ser. No. 15/153,927 filed May 13, 2016.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on May 13, 2016, is named 43104_00_2281_SL.txt and is 1,706 bytes in size.

FIELD OF THE INVENTION

The invention relates to plants and plant parts, in particular spinach plants (*Spinacia oleracea L.*), which are resistant to *Peronospora farinosa f. sp. spinaciae*. The invention also relates to seeds capable of producing *Peronospora farinosa* f. sp. *spinaciae* resistant plants. The invention further relates to methods for obtaining said plants with altered genotypes and seeds thereof, which are resistant to *Peronospora farinosa* f. sp. *spinaciae*.

BACKGROUND OF THE INVENTION

Spinach (*Spinacia oleracea L.*) is a flowering plant from the Amaranthaceae family that is grown as a vegetable. The consumable parts of spinach are the leaves and petioles from the vegetative stage. Spinach is sold loose, bunched, in pre-packed bags, canned, or frozen. There are three basic types of spinach: industry-, fresh and Asiatic spinach. Within these types three different leaf types can be recognized: namely the savoy, semi-savoy and smooth types. Savoy has dark green, crinkly and curly leaves. Flat or smooth leaf spinach has broad, smooth leaves. Semi-savoy is a variety with slightly crinkled leaves. The main market for spinach is baby-leaf. Baby spinach leaves are often of the flat-leaf variety and usually the harvested leaves are not longer than about eight centimeter. These tender, sweet leaves are sold loose rather than in bunches. They are often used in salads, but can also be lightly cooked.

Downy mildew—in spinach caused by the oomycete fungus *Peronospora farinosa f. sp. spinaciae* (formerly known as *P. effusa*)—is a major threat for spinach growers, because it affects the harvested plant parts, namely the leaves. Infection makes the leaves unsuitable for sale and consumption, as it manifests itself phenotypically with yellow lesions on the older leaves and a greyish fungal growth on the abaxial leaf. The infection can spread very rapidly and can occur both in glasshouse and in soil cultivation. The optimal temperature for formation and germination of *P. farinosa f sp. spinaciae* spores is 9 to 12° C., and it is facilitated by a high relative humidity. When spores are deposited on a humid leaf surface they can readily germinate and infect the leaf. Fungal growth is optimal between 8 and 20° C. and a relative humidity of ≥80%, and within 6 and 13 days after infection mycelium growth can be observed. Oospores of *P. farinosa* can survive in the soil for up to 3 years, or as mycelium in seeds or living plants.

In recent years various resistance genes or R-genes have been identified that provide spinach plants with a resistance against downy mildew, as described in e.g. US2013230635, WO2015036378, WO2015036469, and EP2848114. Co-evolution of plant and pathogen has led to an arms race in which a R-gene mediated resistance can be broken down as a consequence of the capability of the pathogen to interact with and modify alternative host targets or the same targets in a different way. In any case, the recognition is lost and infection can be established successfully resulting in disease. In order to re-establish resistance in a plant, a new R-gene has to be introduced which is able to recognize the mode of action of an alternative pathogenicity factor.

This shows that the durability of such R-genes is relatively low, especially since the last few years the development of new races of spinach downy mildew has increased rapidly.

To date 16 pathogenic races of spinach downy mildew (Pfs) have been officially identified and characterized, and many new candidates are observed in the field. The 16 officially recognised races of *Peronospora farinosa* f. sp. *spinaciae*, are designated Pfs:1 to Pfs:16 (Irish et al. Phtypathol. Vol. 98 pg. 894-900, 2008; Plantum NL (Dutch association for breeding, tissue culture, production and trade of seed and young plants) press release, "Benoeming van Pfs:14, een nieuwe fysio van valse meeldauw in spinazie", Sep. 19, 2012; Report Jim Correl (Univ. Arkansas) and Steven Koike (UC Cooperative Extension, Monterey County), "Race Pfs:14—Another new race of the spinach downy mildew pathogen", Sep. 18, 2012; Plantum NL press release, "Denomination of Pfs:15, a new race of downy mildew in spinach", Sep. 2, 2014, Plantum NL press release, "Denomination of Pfs:16, a new race of downy mildew in spinach", Mar. 15, 2016). Races 4 to 15 were identified between 1990 and 2014, while only recently another new Peronospora isolate has been identified, termed UA201519B, which subsequently has been officially named Pfs:16 by the International Working Group on Peronospora (IWGP) (Plantum NL (Dutch association for breeding, tissue culture, production and trade of seed and young plants) press release, "Denomination of Pfs:16, a new race of downy mildew in spinach", Mar. 15, 2016. All 16 officially recognized Pfs races are publicly available from the Department of Plant Pathology, University of Arkansas, Fayetteville, Ark. 72701, USA, and also from NAK Tuinbouw, Sotaweg 22, 2371 GD Roelofarendsveen, the Netherlands.

Given the fact that R-gene mediated resistance provides a resistance of relatively low durability and the fact that the downy mildew pathogen is evolving and adapting more rapidly to these R-genes, there is a need in the art to have resistance sources available which are more durable compared to R-gene mediated resistance.

Next to an R-mediated defense mechanism, a plant can exhibit a more basal form of resistance which may prevent the pathogen from infecting the plant. This non-R-gene mediated form of resistance can be considered as an extremely successful form of defense which in fact is effective for most plant pathogen interactions. Since such a resistance is not based on the kind of interaction and recognition between host and pathogen as is known for R-genes, this defense mechanism provides resistance against a broader spectrum of pathogen races than would normally be expected with R-genes.

Citation or identification of any document in this application is not an admission that such document is available as prior art to the present invention.

SUMMARY OF THE INVENTION

Given the significant advantages of a non-R-gene mediated resistance, it is the object of the present invention to provide a spinach plant resistant to downy mildew, wherein the resistance is caused by a non-R-gene mediated resistance conferring chromosomal interval.

In the research that led to the present invention, new spinach plants were developed which have in their genome a locus capable of providing non-R-gene mediated resistance against downy mildew. The locus of the invention providing broad spectrum resistance is named the p10 locus.

The broad spectrum resistance conferred by the p10 locus in the context of this invention is defined as providing at least an intermediate resistance to the following races of downy mildew (*Peronospora farinosa f. sp. spinaciae*) Pfs: 1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16. The p10 locus that confers broad spectrum resistance onto spinach plants is obtainable by introgression from seeds of which a representative sample was deposited with the NCIMB under NCIMB accession number 42554.

The invention thus relates to a spinach plant which may comprise the p10 locus, which when homozygously present provides at least intermediate resistance to *Peronospora farinosa f. sp. spinaciae* races Pfs:1 to Pfs:16, wherein the locus is as found in plants grown from seeds of which a representative sample was deposited with the NCIMB under accession number 42554.

Spinach plants of the invention, carrying the new source of resistance designated as p10, can be crossed with other spinach plants which may comprise one or more dominant R-genes. In this way an even stronger resistance is obtained and the emergence of new resistance breaking downy mildew strains is slowed down thereby increasing the durability of dominant R-genes. The invention thus relates to a spinach plant exhibiting complete resistance to *Peronospora farinosa* f. sp. *spinaciae* races Pfs:1 to Pfs:16. Such spinach plants suitably comprise the p10 locus and one or more R-genes.

The spinach plant of the invention is obtainable by crossing a first spinach plant with a second spinach plant, wherein one or both of said spinach plants may comprise the p10 resistance locus of the invention, to obtain F1 plants and optionally more generations of spinach plants which may comprise the p10 locus.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

DEPOSIT INFORMATION

The Deposit with NCIMB Ltd, Ferguson Building, Craibstone Estate, Bucksburn, Aberdeen AB21 9YA, UK, on the 24th of Feb. 2016, under deposit accession number 42554 was made and accepted pursuant to the terms of the Budapest Treaty. Upon issuance of a patent, all restrictions upon the deposit will be removed, and the deposit is intended to meet the requirements of 37 CFR § 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION

The present invention thus relates to a spinach plant which may comprise a non R-gene mediated broad spectrum resistance to at least the officially recognized *Peronospora farinosa f. sp. spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16, wherein the resistance is caused by a new locus designated p10 and wherein the resistance caused by the p10 locus is at least of an intermediate level.

In contrast to a resistance mediated by a dominant R-gene, the p10 locus of the invention only provides resistance when homozygously present. Therefore, the resistance conferred by the p10 locus is transferred in a pattern that fits a recessive inheritance. Due to its inheritance the p10 resistance is considered to be a non-R-gene mediated resistance. Furthermore, due to the resistance profile provided by the p10 locus the resistance is regarded to be a broad spectrum resistance.

Therefore, in a particular embodiment the p10 locus is homozygously present, thus providing a spinach plant with at least intermediate resistance against *Peronospora farinosa f. sp. spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16.

In the context of this invention, intermediate resistance is defined as a plant showing only symptoms of chlorosis, or sporulation occurring only on the tips of the cotyledons in the differential seedling test as described herein.

Furthermore, in the context of this invention complete resistance is defined as a plant showing no symptoms in the seedling test as described herein. Complete resistance is also referred to as full resistance.

The presence of the p10 locus in a plant may be detected using a seedling test as described herein. The resistance phenotype is assessable in a disease resistance assay such as the seedling test described herein, as illustrated by the examples.

A seedling test is defined as a test wherein spinach plants are planted in trays containing growth medium, and optionally fertilized twice a week after seedling emergence. Plants are inoculated at the first true leaf stage with a sporangial suspension having a concentration of approximately $2.5 \times 10^5$/ml of one of the pathogenic races of *Peronospora farinosa f. sp. spinaciae* or isolates to be tested. The inoculated plants are placed in a dew chamber at 18° C. with 100% relative humidity for a 24 h period, and then moved to a growth chamber at 18° C. with a 12 h photoperiod for 6 days. After 6 days, the plants are returned to the dew chamber for 24 h to induce sporulation, and subsequently scored for a disease reaction. Preferably, 30 plants per race are tested.

It was further found that the p10 locus of the invention is located on chromosome 1 and flanked by markers SO01770 and SO00979.

The invention thus relates to a spinach plant which may comprise the p10 locus wherein the locus is located on chromosome 1 and is flanked by markers SO01770 and SO00979.

The p10 locus of the invention is located on chromosome 1, and in a plant grown from a seed of which a representative sample was deposited with the NCIMB under NCIMB accession number 42554 the presence of the p10 locus is detectable using marker SO00696 and/or marker SO0305. When crossing a plant carrying the p10 locus with a fully susceptible plant of reference variety Viroflay, i.e. not carrying the p10 locus, the SNPs of markers SO00696 and SO0305 as indicated in bold and underlined in SEQ ID No. 1 and SEQ ID No. 3 respectively (see Table 1) are linked to the presence of the p10 locus. In such a cross the SNPs of markers SO00696 and SO0305 as indicated in bold and underlined in SEQ ID No. 2 and/or SEQ ID No. 4 respectively (see Table 1) are linked to the absence of the p10 locus.

Therefore, the invention relates to a spinach plant which may comprise the p10 locus wherein the locus is located on chromosome 1 and linked to SNP markers as present in SEQ ID No. 1, and/or SEQ ID No. 3.

The deposit is homozygous for the SNPs of SEQ ID No. 1 and SEQ ID No. 3. When the deposit is crossed with a plant of reference variety Viroflay these SNPs are linked to the p10 locus. Therefore, the deposit may function as a reference for the SNPs of SEQ ID No. 1 and SEQ ID No. 3. Hence, a plant of variety Viroflay is homozygous for the SNPs of SEQ ID No. 2 and SEQ ID No. 4.

However, the skilled person is aware of the fact that recombination may unlink a marker in case the marker is not the causal mutation of the trait that it is linked to. Therefore, a plant of the invention which may comprise in its genome the p10 resistance locus is not limited to the presence of any of the SNPs of SEQ ID No. 1 to 8 as described in Table 1.

In one embodiment the invention relates to the use of a spinach plant which may comprise the p10 locus to develop markers linked to the p10 locus. Such a spinach plant may be, but is not limited to, a plant grown from seed of which a representative sample was deposited with the NCIMB on 24$^{th}$ of February 2016 under NCIMB accession number 42554.

In a further embodiment the invention relates to the use of any of the markers SO00696, SO00305, SO01770, and SO00979 as defined in Table 1 to develop new markers that are linked to the p10 locus.

The invention also relates to a method of identifying a spinach plant which may comprise the p10 locus of the invention, the method which may comprise detecting in a spinach plant a marker that is associated with the resistance, wherein the marker is genetically linked within 20 centiMorgan, in particular 15 centiMorgan, more in particular 10 centiMorgan, even more in particular 5 centiMorgan, and most in particular 1 centiMorgan to at least one marker selected from the group consisting of the markers as defined in Table 1. The method may also comprise selecting a plant which may comprise the p10 locus conferring at least intermediate resistance to *Peronospora farinosa* f. sp. *spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16.

In a further embodiment the invention relates to a method of identifying a spinach plant which may comprise the p10 locus of the invention, the method which may comprise detecting in a spinach plant a marker that is associated with the resistance, wherein the marker is genetically linked within 20 centiMorgan, in particular 15 centiMorgan, more in particular 10 centiMorgan, even more in particular 5 centiMorgan, and most in particular 1 centiMorgan to at least one marker selected from the group consisting of SEQ ID No. 1, SEQ ID No. 2, SEQ ID No. 3, and SEQ ID No. 4 as defined in Table 1. The method may also comprise selecting a plant which may comprise the p10 locus conferring at least intermediate resistance to *Peronospora farinosa f. sp. spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16.

In yet a further embodiment the invention relates to a method of identifying a spinach plant which may comprise the p10 locus of the invention, the method which may comprise detecting in a spinach plant a marker that is associated with the resistance, wherein the marker is genetically linked within 20 centiMorgan, in particular 15 centiMorgan, more in particular 10 centiMorgan, even more in particular 5 centiMorgan, and most in particular 1 centiMorgan to at least one marker selected from the group consisting of SEQ ID No. 1, and SEQ ID No. 3 as defined in Table 1. The method may also comprise selecting a plant which may comprise the p10 locus conferring at least intermediate resistance to *Peronospora farinosa* f. sp. *spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16.

In one embodiment the invention relates to a spinach plant which may comprise the p10 locus, which plant is obtainable by crossing a first spinach plant with a second spinach plant, wherein at least one of the said plants may comprise the p10 locus, wherein the said locus is as found in plants grown from seeds of which a representative sample was deposited with the NCIMB under accession numbers NCIMB 42554, or a progeny plant thereof carrying the p10 locus, and selecting, preferably in the F2 generation, for resistant plants using a disease test, e.g. the seedling test as described herein, and/or by selecting downy mildew resistant plants using any one of the molecular markers in Table 1.

There are many different marker systems available to the skilled artisan, these include but are not limited to SNPs, AFLP markers, RFLP markers, SSRs, RAPD markers, or isozyme markers. Markers that are genetically linked to or correlated with the p10 locus can be utilized (e.g. Acquaah G., Principles of Plant Genetics and Breeding, 2012, West Sussex UK). Methods to isolate, develop and utilize such markers are known in the art.

As used herein, linkage of two nucleic acid sequences, including a nucleic acid marker sequence and a nucleic acid sequence of a genetic determinant such as the p10 locus, may be genetic or physical or both.

In the absence of molecular markers or in the event that recombination between the molecular markers and the p10 locus has taken place and the markers are thus not predictive anymore for the presence of the p10 locus, equivalence of a genetic determinant with the p10 locus may still be determined by an allelism test. To perform an allelism test, material that is homozygous for the known locus, i.e. a tester plant, is crossed with material that is homozygous for the determinant that is to be tested. This latter plant is referred to as the donor plant. The donor plant to be tested should be or should be made homozygous for the determinant to be tested. The skilled person knows how to obtain a plant that is homozygous for the determinant to be tested. When in the F2 of the cross between a donor plant and a tester plant no segregation for the phenotype related to the locus of the invention is observed, the determinant of the donor plant and the known locus of the tester plant have been proven to be equivalent. The phenotype that should be observed is at least an intermediate resistance to the following races of downy mildew (*Peronospora farinosa f. sp. spinaciae*) Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16. A tester plant may be, but is not limited to, a plant grown from seed deposited with the NCIMB under accession number NCIMB 42554.

In one embodiment, the invention relates to a spinach plant (*Spinacia oleracea*) which may comprise the p10 locus that leads to a broad spectrum resistance against downy mildew (*Peronospora farinosa f. sp. spinaciae*) races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16, which locus may be comprised in or is equivalent to the p10 locus as found in a spinach plant representative seed of which was deposited with the NCIMB under accession number NCIMB 42554 as may be determined using an allelism test, in particular as described above.

In one aspect the invention relates to a spinach plant which may comprise the p10 locus, obtainable by crossing a spinach plant with a plant grown from a seed of deposit NCIMB 42554 to produce F1 progeny, selfing the F1 progeny to produce F2 progeny and selecting from the F2 progeny the plants that shows at least intermediate resistance to *Peronospora farinosa f. sp. spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16 as plants having obtained the p10 broad spectrum resistance locus.

The invention further relates to a spinach plant which may comprise the p10 broad spectrum resistance locus, wherein the p10 locus upon introduction thereof in a spinach plant that is susceptible to all races of *Peronospora farinosa* f. sp. *spinaciae* induces a resistance profile that consists of at least intermediate resistance to races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16.

The word "trait" in the context of this application refers to the phenotype of the plant, in the present invention to a particular resistance profile. A resistance profile is a combination of a number of races or isolates against which the plant shows resistance. More in particular the word "trait" refers to a phenotype caused by the homozygous presence of the p10 locus of the invention which is at least intermediate resistance to *Peronospora farinosa* f. sp. *spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16. The term "genetic determinant" or "locus" is used for the genetic information in the genome of the plant that causes the trait of the invention. When a plant shows the trait of the invention, its genome may comprise the genetic determinant or locus homozygously. In the context of this invention "p10 locus", "broad spectrum resistance locus" and "genetic determinant" may be used interchangeably.

It is clear that the parent that provides the trait of the invention is not necessarily a plant grown directly from the deposited seeds. The parent may also be a progeny plant from the seed or a progeny plant from seeds that are identified to have the trait of the invention by other means.

In one embodiment the plant of the invention, i.e. a plant which may comprise the p10 locus, is an agronomically elite spinach plant.

In the context of this invention an agronomically elite spinach plant is a plant having a genotype that as a result of directed crossing and selection by human intervention results into an accumulation of distinguishable and desirable agronomic traits that allow a producer to harvest a product of commercial significance.

In the course of breeding a new spinach plant carrying the broad spectrum resistance locus of the invention, desirable agronomic traits may be introduced into said spinach plant independently of the p10 locus. As used herein, "desirable traits" include but are not limited to e.g. improved yield, leaf shape, leaf size, leaf number, leaf color, seed number, seed size, plant vigor, plant height, bolting speed, and resistance to one or more diseases or disease causing organisms. Any one of these desirable traits may be combined with the p10 locus.

In a further embodiment the spinach plant of the invention may exhibit complete resistance against one or more of the following *Peronospora farinosa* f. sp. *spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16 due to the presence of one or more R-genes, e.g. RPFJ, RPF2, RPF3, RPF4, RPF5 and RPF6 (Feng et al. Identification of new races and deviating strains of the spinach downy mildew pathogen *Peronospora farinosa* f. sp. *spinaciae* 2014 Plant Disease 98(1): 145-152). The spinach plant may further be resistant or tolerant to one of the following diseases: CMV, Colletotrichum, Cladosporium, and Fusarium. Next to any of the aforementioned resistances the spinach plant of the invention may comprise a delayed or enhanced bolting phenotype. The spinach plant of the invention may also comprise one of the following leaf shapes: savoy, semi-savoy or smooth leaves. The leaves of the plant may independent of their shape comprise elevated concentrations of the red pigment betacyanin in the petiole, veins and/or between the veins of the leaves (see e.g. US20140272083). Next to the aforementioned traits a spinach plant of the invention may comprise a multileaf characteristic (see e.g. US20120054894). For example, the invention in one embodiment relates to an agronomically elite hybrid spinach variety that is resistant to *Peronospora farinosa* f. sp. *spinaciae* races Pfs:1-13 and Pfs:15 and intermediately resistant to Pfs:14 and Pfs:16 due to the presence of two R-genes and the p10 locus, respectively, and further resistant to CMV, showing slow bolting and having smooth leaves. Another example of such an agronomically elite hybrid variety is a variety resistant to *Peronospora farinosa* f. sp. *spinaciae* races Pfs:1-9 and pfs:11-16 and intermediately resistant to Pfs:10 due to the presence of two R-genes and the p10 locus, having a fast growing phenotype, but relatively slow bolting, and well suited for the industrial harvest segment.

In yet a further embodiment the agronomically elite spinach plant of the invention is an inbred line or a hybrid.

As used herein, a plant of an inbred line is a plant of a population of plants that is the result of three or more rounds of selfing, or backcrossing; or which plant is a double haploid. An inbred line may e.g. be a parent line used for the production of a commercial hybrid.

As used herein, a hybrid plant is a plant which is the result of a cross between two different plants having different genotypes. More in particular, a hybrid plant is the result of a cross between plants of two different inbred lines, such a hybrid plant may e.g. be a plant of a commercial $F_1$ hybrid variety.

In one embodiment the plant which may comprise the p10 locus is an $F_1$ hybrid variety.

Furthermore, the invention relates to hybrid seed that may be grown into a spinach plant which may comprise the p10 locus and to a method for producing such hybrid seed which may comprise crossing a first parent spinach plant with a second parent spinach plant and harvesting the resultant hybrid seed, wherein the first parent plant and/or the second parent plant may comprise the p10 locus homozygously, and growing said hybrid seeds into hybrid spinach plants which may comprise the p10 locus either heterozygously or homozygously.

According to a further aspect thereof, the invention relates to propagation material which may comprise the p10 locus. In one embodiment, the propagation material is suitable for sexual reproduction. Such propagation material may comprise for example a microspore, pollen, an ovary, an ovule, an embryo sac and/or an egg cell. In another embodiment, the propagation material is suitable for vegetative reproduction. Such propagation material may comprise for example a cutting, a root, a stem, a cell, a protoplast, and/or a tissue culture of regenerable cells. A part of the plant that is suitable for preparing a tissue culture is in particular a leaf, pollen, an embryo, a cotyledon, a hypocotyl, a meristematic cell, a root tip, an anther, a flower, a seed or a stem.

In one embodiment, such propagation material is formed by a seed of a spinach plant of the invention, wherein the plant that may be grown from the seed is carrying the p10 locus of invention.

In a further embodiment, such propagation material is formed by a seed of a spinach plant of the invention, wherein the plant that may be grown from the seed may comprise the p10 locus of the invention in a homozygous state.

The invention further relates to a cell of a spinach plant of the invention, which cell may comprise the p10 locus of the invention, wherein said locus is as found in a spinach plant, representative seeds of which were deposited under NCIMB accession number 42554. The said cell thus may comprise the genetic information encoding the broad spectrum resistance, in particular it may comprise genetic information which is substantially identical, preferably completely identical to the genetic information encoding the said broad spectrum resistance trait of the spinach plant, representative seeds of which were deposited under NCIMB accession number 42554. Preferably, the cell of the invention is part of a plant or plant part, but the cell may also be in isolated form.

The invention also relates to the use of seeds that were deposited under NCIMB accession number 42554 for transferring at least intermediate resistance to *Peronospora farinosa f. sp. spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16 into an agronomically valuable spinach plant by crossing a plant grown from said deposited seed with another plant which may comprise other agronomically desirable traits.

The invention also relates to progeny of the plants, cells, tissues and seeds of the invention. Such progeny can in itself be plants, cells, tissues or seeds. As used herein the word "progeny" is intended to mean the first and all further descendants from a cross with a plant of the invention that may comprise the p10 locus. "Progeny" encompasses all plants that carry the p10 locus in a heterozygous or homozygous state and are obtained from other plants or progeny of plants of the invention by vegetative propagation or multiplication. In case the progeny plant may comprise the p10 locus in a homozygous form the plant exhibits at least an intermediate resistance against *Peronospora farinosa* f. sp. *spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16.

The said progeny plants may comprise an introgression fragment that may comprise the p10 locus, wherein the said introgression fragment is obtainable from a spinach plant of which representative seed is deposited with the NCIMB under NCIMB accession number 42554. The resistance trait thus has a genetic basis in the genome of a spinach plant, and using the disease resistance assay as described herein, spinach plants may be identified as being plants of the invention. It is understood that a parent plant that provides the trait of the invention is not necessarily a plant grown directly from the deposited seeds. The parent may also be a progeny plant from the seed, or a progeny plant from seeds that are identified to have (or to have acquired) the trait of the invention by other means.

In one embodiment, the invention relates to a spinach plant that carries the trait of the invention and that has acquired the said trait by introduction of the genetic information that is responsible for the trait from a suitable source, either by conventional breeding, or genetic modification, in particular by cis-genesis or trans-genesis. Cis-genesis is genetic modification of plants with a natural gene, encoding an (agricultural) trait from the crop plant itself or from a sexually compatible donor plant. Trans-genesis is genetic modification of a plant with a gene from a non-crossable species or with a synthetic gene.

In one embodiment, the source from which the genetic information is acquired is formed by plants grown from the deposited seeds, or by sexual or vegetative descendants thereof.

The invention also relates to the germplasm of plants of the invention. The germplasm is constituted by all inherited characteristics of an organism and according to the invention encompasses at least the p10 locus of the invention. The germplasm can be used in a breeding program for the development of downy mildew resistant spinach plants.

In one aspect the invention relates to a method for the production of a spinach plant which may comprise a broad spectrum resistance against downy mildew (*Peronospora farinosa f. sp. spinaciae*) races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16 caused by the p10 locus, which may comprise: (a) crossing a plant which may comprise the p10 locus of the invention with another plant; (b) selfing the resulting F1 for obtaining F2 plants; (c) selecting in the F2 for plants which are at least intermediately resistant to downy mildew (*Peronospora farinosa* f. sp. *spinaciae*) races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16; (d) optionally performing one or more additional rounds of selfing or crossing, and subsequently selecting, for a plant which may comprise said broad spectrum resistance against *Peronospora farinosa* f. sp. *spinaciae*. The invention also includes a spinach plant produced by this method.

More particularly, the invention relates to a method for introgressing the p10 locus into an agronomically elite spinach plant by means of backcrossing, which may comprise: (a) crossing a spinach plant which may comprise the p10 locus with an agronomically elite spinach plant not comprising said locus in its genome to produce F1 progeny; (b) selecting in the F1 and/or F2 for a progeny plant which may comprise the p10 locus; (c) crossing the progeny plant which may comprise the p10 locus with the said agronomically elite spinach plant to produce backcross progeny; and (d) selecting backcross progeny which may comprise the p10 locus; and (e) optionally, repeating steps (c) and (d) one or more times. In particular step (e) may be repeated from 1 up to 10 times. The invention also includes a spinach plant produced by this method.

More in particular the invention provides a method of introducing a desired trait into an agronomically elite spinach plant which is carrying the p10 broad spectrum resistance locus, which may comprise: (a) crossing said agronomically elite spinach plant with a second spinach plant that may comprise a desired trait to produce F1 progeny; (b) selecting in the F1 and/or F2 for a progeny plant which may comprise said p10 locus and the desired trait; (c) crossing the selected progeny plant with the agronomically elite parent carrying the p10 locus, to produce backcross progeny; (d) selecting backcross progeny which may comprise the desired trait and the broad spectrum resistance as conferred by the p10 locus; and (e) optionally repeating steps (c) and (d) one or more times in succession to produce subsequent generations of backcross progeny that may comprise the desired trait and the broad spectrum resistance as conferred by the p10 locus. The invention also includes a spinach plant produced by this method.

It is clear that the parent that provides the trait of the invention is not necessarily a plant grown directly from the deposited seeds. The parent can e.g. also be a progeny plant from the seed or a progeny plant from seeds that are identified to have the trait of the invention by other means.

The invention also relates to harvested leaves of spinach plants of the invention, and to a food product which may comprise harvested leaves of spinach plants of the invention, either in natural or in processed form.

Spinach leaves are for example sold in packaged form, including without limitation as pre-packaged spinach leaves, or as a processed product in a salad which may comprise spinach leaves. Mention of such a package is e.g. made in U.S. Pat. No. 5,523,136, which provides packaging film, and packages from such packaging film, including such packaging containing leafy produce, and methods for making and using such packaging film and packages, which are suitable for use with the spinach leaves of the invention. Thus, the invention also provides the use of and methods for making and using the leaves of the spinach plant of the invention, as well as leaves of spinach plants derived from the invention. The invention further relates to a container which may comprise one or more plants of the invention, or one or more spinach plants derived from a plant of the invention, in a growth substrate for harvest of leaves from the plant, in a domestic environment. This way the consumer may pick very fresh leaves for use in salads, when the plant is in a ready-to-harvest condition. Spinach may also be sold as a food product that is already cooked or sautéed and optionally frozen.

The invention further involves a method of determining the genotype of a plant of the invention, representative seed of which has been deposited under NCIMB Accession No. 42554, or a first generation progeny plant thereof, which may comprise obtaining a sample of nucleic acids from said plant and a reference plant not comprising the genetic determinant of the invention and detecting in the nucleic acids of said samples a plurality of polymorphisms. This method may additionally comprise the step of storing the results of detecting the plurality of polymorphisms on a computer readable medium. The plurality of polymorphisms are indicative of and/or give rise to the presence of the p10 locus.

There are various ways of obtaining genotypic data from a nucleic acid sample. Genotypic data may be gathered which is specific for certain phenotypic traits (e.g. gene sequences), but also patterns of random genetic variation may be obtained to construct a so-called DNA fingerprint. Depending on the technique used a fingerprint may be obtained that is unique for a spinach plant carrying the resistance allele of the invention. Obtaining a unique DNA fingerprint depends on the genetic variation present in a variety and the sensitivity of the fingerprinting technique. A technique known in the art to provide a good fingerprint profile is called AFLP fingerprinting technique (See generally U.S. Pat. No. 5,874,215), but there are many other marker based techniques, such as RFLP (or Restriction fragment length polymorphism), SSLP (or Simple sequence length polymorphism), RAPD (or Random amplification of polymorphic DNA) VNTR (or Variable number tandem repeat), Microsatellite polymorphism, SSR (or Simple sequence repeat), STR (or Short tandem repeat), SFP (or Single feature polymorphism) DarT (or Diversity Arrays Technology), RAD markers (or Restriction site associated DNA markers) (e.g. Baird et al. PloS One Vol. 3e3376, 2008; Semagn et al. African Journal of Biotechnology Vol. 5 number 25 pp. 2540-2568, 29 Dec., 2006). Nowadays, sequence-based methods are utilizing Single Nucleotide Polymorphisms (SNPs) that are randomly distributed across genomes, as a common tool for genotyping (e.g. Elshire et al. PloS One Vol. 6: e19379, 2011; Poland et al. PloS One Vol. 7: e32253; Truong et al. PloS One Vol. 7 number 5: e37565, 2012).

With any of the aforementioned genotyping techniques, polymorphisms may be detected when the genotype and/or sequence of the plant of interest is compared to the genotype and/or sequence of one or more reference plants. As used herein, the genotype and/or sequence of a reference plant may be derived from, but is not limited to, any one of the following: parental lines, closely related plant varieties or species, complete genome sequence of a related plant variety or species, or the de novo assembled genome sequence of one or more related plant varieties or species. For example, it is possible to detect polymorphisms for the presence or absence of the p10 locus by comparing the genotype and/or the sequence of a spinach plant carrying the resistance conferring allele, representative seed of which has been deposited under NCIMB Accession No. 42554, with the genotype and/or the sequence of one or more reference plants. The reference plant(s) used for comparison in this example may for example be, but is not limited to, any of the spinach varieties mentioned in Table 2 and/or parent lines, ancestor, or progeny plants thereof.

The polymorphism or polymorphisms revealed by these techniques may be used to establish links between genotype and phenotype. The polymorphisms may thus be used to predict or identify certain phenotypic characteristics, e.g. the resistance provided by the p10 locus, individuals, or even species. The polymorphisms are generally called markers. It is common practice for the skilled artisan to apply molecular DNA techniques for generating polymorphisms and creating markers.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer searchable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphisms of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

MARKER INFORMATION

SEQ ID No. 1 and SEQ ID No. 3 represent the alleles of markers SO00696 and SO00305 that in the genome of seeds of the deposit NCIMB 42554 are linked to the p10 locus of the invention. Therefore, the homozygous presence of SEQ ID No. 1 and SEQ ID No. 3 in the genome of seeds of the deposit NCIMB 42554 is linked to the resistance conferred by the p10 locus, which is an at least intermediate resistance to *Peronospora farinosa* f. sp. *spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16.

The sequences of SEQ ID No. 2 and SEQ ID No. 4 represent the wildtype alleles for markers SO00696 and SO00305 as present in the fully susceptible variety Viroflay, respectively.

For markers SO00696 and SO00305 the nucleotides that are different between the marker allele linked to the p10 allele and the marker allele linked to the susceptible allele in a plant of variety Viroflay are underlined and in bold in Table 1. For SO00696 this difference is a SNP on position 26, wherein SEQ ID No. 1 on position 26 has a G and SEQ ID No. 2 on position 26 has an A. For SO00305 this difference is a SNP on position 33, wherein SEQ ID No. 3 on position 33 has a T and SEQ ID No. 4 on position 33 has an A.

The SNPs indicated in these sequences (the nucleotides in bold and underlined) may be used as molecular markers for detecting the presence of the p10 locus in the progeny of a cross between a plant of reference variety Viroflay and a plant comprising the p10 locus, which plant may be a plant grown from seeds of which a representative sample was deposited with the NCIMB under NCIMB accession number 42554.

The nucleotides that are different between the two marker alleles of markers SO01770, and SO00979 are underlined and in bold in Table 1. In the case of marker SO01770 the marker allele (SEQ ID No. 6) has a single nucleotide deletion at the position where marker allele (SEQ ID No. 5) has a C that is underlined and in bold (position 58 of SEQ ID No. 5). For SO00979 this is a SNP on position 24, wherein SEQ ID No. 7 on position 24 has a T and SEQ ID No. 8 on position 24 has a C.

TABLE 1

Marker information

| Marker name | Seq ID No. | Sequence marker |
|---|---|---|
| SO00696 | SEQ ID No. 1 | CCTAATGGCTCTAAGGTTTCATCAAGACCTAAGAAAGCAGAAAAAATGCAGAAGCCCA |
|  | SEQ ID No. 2 | CCTAATGGCTCTAAGGTTTCATCAAAACCTAAGAAAGCAGAAAAAATGCAGAAGCCCA |
| SO00305 | SEQ ID No. 3 | ATTGTACAAATTTCAGAAACAGTTATAACCAATTTCAGATAATAAACAGATTTCCACTTCACATATTTCTTACCTCAARC |
|  | SEQ ID No. 4 | ATTGTACAAATTTCAGAAACAGTTATAACCAAATTCAGATAATAAACAGATTTCCACTTCACATATTTCTTACCTCAARC |
| SO01770 | SEQ ID No. 5 | CATAAACATTCCGTATGAGTAGTACTCTATTTGTCTCAAAAAGAAAATTGAAAATTGCCCTAGTCGAAATTTTATCTGCACTA |
|  | SEQ ID No. 6 | CATAAACATTCCGTATGAGTAGTACTCTATTTGTCTCAAAAAGAAAATTGAAAATTGCCTAGTCGAAATTTTATCTGCACTA |

TABLE 1-continued

Marker information

| Marker name | Seq ID No. | Sequence marker |
|---|---|---|
| SO00979 | SEQ ID No. 7 | GATGCTCAGCCGCTCACCAGTATTTG GTTTTCATGAGCCAAAAACTGGA |
|  | SEQ ID No. 8 | GATGCTCAGCCGCTCACCAGTATCTG GTTTTCATGAGCCAAAAACTGGA |

The invention will be further illustrated in the following Examples. In these Examples reference is made to the following figures.

EXAMPLES

Example 1

Testing for the p10 locus in spinach plants

The resistance to downy mildew infection was assayed as described by Irish et al. (2008; Phytopathol. 98: 894-900), using a differential set. Spinach plants of the invention comprising the p10-locus homozygously were planted along with spinach plants from different other genotypes (see Table 2) in trays containing Scotts Redi-Earth medium, and fertilized twice a week after seedling emergence with Osmocote Peter's (13-13-13) fertilizer (Scotts). Plants were inoculated with a sporangial suspension (2.5×105/ml) of a pathogenic race of Peronospora farinosa f. sp. spinaciae at the first true leaf stage. In this manner, 16 pathogenic races were tested (as shown in Table 2).

The inoculated plants were placed in a dew chamber at 18° C. with 100% relative humidity for a 24 h period, and then moved to a growth chamber at 18° C. with a 12 h photoperiod for 6 days. After 6 days, the plants were returned to the dew chamber for 24 h to induce sporulation, and they were scored for disease reaction.

Plants were scored as resistant, intermediately resistant, or susceptible based on symptoms of chlorosis and signs of pathogen sporulation on the cotyledons and true leaves, as described by Irish et al. (2007; Plant Dis. 91: 1392-1396). Plants exhibiting neither sporulation nor chlorosis were considered resistant, plants exhibiting only chlorosis, or sporulation occurring only on the tips of the cotyledons were considered intermediately resistant, and plants exhibiting sporulation covering a substantive part of the cotelydon were considered susceptible.

Table 2 shows the differential set of spinach downy mildew races and the resistance of various spinach varieties (hybrids) to each one of these pathogenic races. A susceptible reaction is scored as "+" (indicating a successful infection by the fungus, with sporulation occurring on the entire cotyledon), and resistance is depicted as "−" (absence of sporulation on the cotyledons). A weak resistance response is indicated as "(−)", which in practice means a reduced level of infection (plants exhibiting only chlorosis, or sporulation occurring only on the tips of the cotyledons in the differential seedling test). The p10 line in Table 2 is a line exhibiting the broad spectrum resistance of the present invention.

TABLE 2

| | plants | | | | | | | | | | | | | |
|---|---|---|---|---|---|---|---|---|---|---|---|---|---|---|
| Races | Viroflay | Resistoflay | Califlay | Clermont | Campania | Boeing | Lion | Lazio | Whale | Polka | Pigeon | Caladonia | Meerkat | p10 line |
| Pfs: 1 | + | − | − | − | − | − | − | − | − | − | − | − | − | (−) |
| Pfs: 2 | + | − | + | − | − | − | − | − | − | − | − | − | − | (−) |
| Pfs: 3 | + | + | − | − | − | − | − | − | − | − | − | − | − | (−) |
| Pfs: 4 | + | + | + | − | − | − | − | − | (−) | + | − | − | − | (−) |
| Pfs: 5 | + | + | − | + | − | − | − | − | − | − | − | − | − | (−) |
| Pfs: 6 | + | + | + | + | + | − | − | − | (−) | + | − | − | − | (−) |
| Pfs: 7 | + | + | + | + | − | − | − | − | (−) | + | − | − | − | (−) |
| Pfs: 8 | + | + | − | + | + | + | − | − | − | − | − | − | − | (−) |
| Pfs: 9 | + | + | − | + | + | − | − | − | − | − | − | − | − | (−) |
| Pfs: 10 | + | + | + | + | + | + | + | − | + | + | − | − | − | (−) |
| Pfs: 11 | + | + | − | + | − | − | − | + | − | − | − | − | − | (−) |
| Pfs: 12 | + | + | − | + | + | + | − | + | − | − | − | − | − | (−) |
| Pfs: 13 | + | + | + | + | (−) | − | − | + | + | (−) | − | − | − | (−) |
| Pfs: 14 | + | + | − | + | + | + | − | + | (−) | − | + | − | − | (−) |
| Pfs: 15 | + | + | + | − | − | − | − | + | + | − | + | − | − | (−) |
| Pfs: 16 | + | + | − | + | − | − | − | + | − | − | + | − | + | (−) |

Example 2

Introduction of the p10 resistance locus into other spinach plants

A plant of the invention was crossed (as a father) with a plant of variety Viroflay, to obtain an F1. Thirty plants of the F1 population were tested for resistance to Peronospora race 13, as described in example 1. None of the 30 plants showed the resistance pattern of the invention, i.e. all plants were susceptible to Pfs:13.

Five F1 plants were selfed and from each plant 40 seeds were sown and an F2 population of 196 plants was obtained. The F2 plants were tested for resistance to Peronospora race 13 as described in example 1. It was observed that 42 plants showed resistance or intermediate resistance against pfs:13. The remaining 154 plants were all susceptible for Pfs:13. A Chi-square tests confirmed that the observed segregation in the F2 populations was consistent with a 1:3 segregation of the p10 locus, as assayed here with resistance to Peronospora race 13. In other words the p10 locus is inherited in a pattern that fits a monogenic recessive inheritance.

TABLE 3

| Population # | strain | R | IR | S |
|---|---|---|---|---|
| Population 1 | Pfs: 1 | 30 | 0 | 0 |
| Population 2 | Pfs: 2 | 29 | 1 | 0 |
| Population 3 | Pfs: 3 | 26 | 0 | 0 |
| Population 4 | Pfs: 4 | 30 | 0 | 0 |
| Population 5 | Pfs: 5 | 30 | 0 | 0 |
| Population 6 | Pfs: 6 | 30 | 0 | 0 |
| Population 7 | Pfs: 7 | 30 | 0 | 0 |
| Population 8 | Pfs: 8 | 25 | 4 | 1 |
| Population 9 | Pfs: 9 | 21 | 1 | 3 |
| Population 10 | Pfs: 10 | 28 | 2 | 0 |
| Population 11 | Pfs: 11 | 29 | 1 | 0 |
| Population 12 | Pfs: 12 | 30 | 0 | 0 |
| Population 13 | Pfs: 13 | 30 | 0 | 0 |
| Population 14 | Pfs: 14 | 29 | 1 | 0 |
| Population 15 | Pfs: 15 | 25 | 4 | 1 |
| Population 16 | Pfs: 16 | 28 | 2 | 0 |

The best scoring plant of the F2 population was selfed to produce an F3 population. 16×30 seeds of the F3 seedlot were germinated for testing against the 16 recognized Peronospora races (see Table 3). These results show that the resistance conferred by the p10 locus is indeed a broad spectrum resistance against at least Pfs:1-16.

Example 3

Marker assisted introduction of the p10 resistance locus into other spinach plants A plant of the invention was crossed (as a father) with a plant of variety Viroflay, to obtain an F1.

Four F1 plants were selfed and from each plant 24 seeds were sown to form four F2 populations of in total 96 plants.

From these plants DNA was extracted and purified using standard available protocols.

On these samples, together with DNA samples of both parents (as negative and positive control), a KASPar assay (Kompetitive Allele Specific PCR; see e.g. Semagn et al., 2014. Molecular Breeding 33 (1): 1-14) was run for two markers 5000696 and 5000305.

For the positive control the scoring of these markers was in accordance with the SNPs as present in SEQ ID No. 1 and SEQ ID No. 3 (as indicated in Table 1). For Viroflay (negative control) the scoring of these markers was in accordance with the SNPs as present in SEQ ID No. 2 and SEQ ID No. 4 (as indicated in Table 1).

From the total of 96 plants that formed the F2 population, 23 plants had a scoring conform the positive control plant. The remaining 73 plants showed the marker score as found in the negative control plant.

Subsequently the 23 plants for which the markers scored in accordance with the SNPs as present in SEQ ID No. 1 and SEQ ID No. 3 were selfed to form 23 F3 populations containing 120 plants each. Each F3 population was subjected to a seedling test (as described in example 1). In the seedling test the plants were tested for resistance against races Pfs:3, Pfs:6, Pfs:10 and Pfs:14. All these plants were scored as at least intermediately resistant for these four *Peronospora* races.

What is claimed is:

1. An agronomically elite spinach plant comprising a downy mildew resistance contributing locus designated p10 located on chromosome 1,
    wherein said locus when homozygously present provides at least intermediate resistance to *Peronospora farinosa* f sp. *spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16,
    wherein the p10 locus is as found in a plant grown from a seed of which a representative sample was deposited with the NCIMB under Accession No. 42554, and
    wherein the p10 locus in a plant grown from a seed of which a representative sample was deposited with the NCIMB under NCIMB Accession No. 42554 is located between marker S000979 having SEQ ID NO: 7 or 8 and marker SO01770 having SEQ ID NO: 5 or 6.

2. The spinach plant of claim 1 wherein the p10 locus in a plant grown from a seed of which a representative sample was deposited with the NCIMB under NCIMB Accession No. 42554 is linked to the SNPs in SEQ ID NO: 1, and/or SEQ ID NO: 3.

3. A spinach plant as claimed in claim 1, wherein the p10 locus is homozygously present.

4. The agronomically elite spinach plant of claim 1 wherein said plant is an inbred line or a hybrid.

5. The spinach plant of claim 1, wherein the spinach plant exhibits complete resistance to *Peronospora farinosa* f sp. *spinaciae* races Pfs:1-16.

6. A propagation material comprising the p10 locus of claim 1, wherein the propagation material comprises a microspore, a pollen, an ovary, an ovule, an embryo, an embryo sac, an egg cell, a cutting, a root, a root tip, a hypocotyl, a cotyledon, a stem, a leaf, a flower, an anther, a seed, a meristematic cell, a protoplast, a cell, or a tissue culture thereof.

7. A cell of a spinach plant, wherein the cell comprises the p10 locus of claim 1.

8. A spinach seed comprising in its genome the p10 locus of claim 1.

9. The seed of claim 8, wherein the seed gives rise to an agronomically elite spinach plant.

10. A harvested leaf of a spinach plant as claimed in claim 1.

11. A food product comprising the harvested leaf of claim 10.

12. A container comprising the harvested leaf of the spinach plant as claimed in claim 1.

13. A method of selecting a spinach plant comprising the p10 locus of claim 1, the method comprising
   detecting in a spinach plant a marker having SEQ ID NO: 1 and/or SEQ ID NO: 3, or a marker associated with the p10 locus wherein the marker is genetically linked within 20 centiMorgan to markers having SEQ ID NO: 1, SEQ ID NO: 3, SEQ ID NO: 5, SEQ ID NO: 6, SEQ ID NO: 7, and/or SEQ ID NO: 8 and
   selecting a spinach plant that comprises said marker as a spinach plant comprising the p10 locus.

14. The method of claim 13, further comprising performing a phenotypic assay for *Peronospora farinosa* f sp. *spinaciae* resistance to select a spinach plan resistant to *Peronospora farinosa* f sp. *spinaciae*.

15. A method for producing a spinach plant comprising at least intermediate resistance to *Peronospora farinosa* f sp. *spinaciae* Pfs:1-16, comprising:
   (a) crossing a plant comprising the p10 of claim 1, with another plant;
   (b) performing one or optionally more rounds of selfing and/or crossing;
   (c) selecting after each round of selfing or crossing for a plant that comprises at least intermediate resistance to *Peronospora farinosa* f sp. *spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16.

16. A method of producing a hybrid spinach seed comprising
   crossing a first parent spinach plant with a second parent spinach plant and
   harvesting the resultant hybrid spinach seed,
   wherein said first parent spinach plant and/or said second parent spinach plant comprises the p10 locus of claim 1.

17. A method of determining the genotype of a spinach plant comprising the p10 locus of claim 1, or a first or second generation progeny thereof, comprising
   obtaining a sample of nucleic acids from said plant,
   comparing said nucleic acids to a sample of nucleic acids obtained from a reference plant, and
   detecting a plurality of polymorphisms between the two nucleic acid samples,
   wherein one or more of the detected polymorphisms are indicative of the presence of the p10 locus of claim 1.

18. The method of claim 17 additionally comprising the step of storing the results of detecting the plurality of polymorphisms on a computer readable medium, or transmitting the results of detecting the plurality of polymorphisms.

19. The spinach plant of claim 1, which is a plant grown from seed having been deposited under NCIMB Accession No. 42554.

* * * * *

UNITED STATES PATENT AND TRADEMARK OFFICE
CERTIFICATE OF CORRECTION

PATENT NO. : 11,751,523 B2
APPLICATION NO. : 16/223491
DATED : September 12, 2023
INVENTOR(S) : Johannes Geert Jan Feitsma et al.

It is certified that error appears in the above-identified patent and that said Letters Patent is hereby corrected as shown below:

On the Title Page

(71) Applicant should read as follows:
RIJK ZWAAN ZAADTEELT EN ZAADHANDEL B.V., De Lier (NL)

In the Claims

Claim 1 should read as follows:
1. An agronomically elite spinach plant comprising a downy mildew resistance contributing locus designated p10 located on chromosome 1, wherein said locus when homozygously present provides at least intermediate resistance to Peronospora farinosa f. sp. spinaciae races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16, wherein the p10 locus is as found in a plant grown from a seed of which a representative sample was deposited with the NCIMB under Accession No. 42554, and wherein the p10 locus in a plant grown from a seed of which a representative sample was deposited with the NCIMB under NCIMB Accession No. 42554 is located between marker SO00979 having SEQ ID NO: 7 or 8 and marker SO01770 having SEQ ID NO: 5 or 6.

Claim 5 should read as follows:
5. The spinach plant of claim 1, wherein the spinach plant exhibits complete resistance to Peronospora farinosa f. sp. spinaciae races Pfs:1-16.

Claim 14 should read as follows:
14. The method of claim 13, further comprising performing a phenotypic assay for Peronospora farinosa f. sp. spinaciae resistance to select a spinach plan resistant to Peronospora farinosa f. sp. spinaciae.

Claim 15 should read as follows:
15. A method for producing a spinach plant comprising at least intermediate resistance to Peronospora farinose f. sp. spinaciae Pfs:1-16, comprising: (a) crossing a plant comprising the p10 of claim 1, with Signed and Sealed this
Sixth Day of February, 2024

Katherine Kelly Vidal
*Director of the United States Patent and Trademark Office* another plant; (b) performing one or optionally more rounds of selfing and/or crossing; (c) selecting after each round of selfing or crossing for a plant that comprises at least intermediate resistance to Peronospora farinosa f. sp. spinaciae races Pfs:1, Pfs:2, Pfs:3, Pfs:4, Pfs:5, Pfs:6, Pfs:7, Pfs:8, Pfs:9, Pfs:10, Pfs:11, Pfs:12, Pfs:13, Pfs:14, Pfs:15 and Pfs:16.

SEQUENCE LISTING

```
<160> NUMBER OF SEQ ID NOS: 8

<210> SEQ ID NO 1
<211> LENGTH: 58
<212> TYPE: DNA
<213> ORGANISM: Spinacia oleracea

<400> SEQUENCE: 1
cctaatggct ctaaggtttc atcaagacct aagaaagcag aaaaaatgca gaagccca    58

<210> SEQ ID NO 2
<211> LENGTH: 58
<212> TYPE: DNA
<213> ORGANISM: Spinacia oleracea

<400> SEQUENCE: 2
cctaatggct ctaaggtttc atcaaaacct aagaaagcag aaaaaatgca gaagccca    58

<210> SEQ ID NO 3
<211> LENGTH: 80
<212> TYPE: DNA
<213> ORGANISM: Spinacia oleracea

<400> SEQUENCE: 3
attgtacaaa tttcagaaac agttataacc aatttcagat aataaacaga tttccacttc    60
acatatttct tacctcaarc                                               80

<210> SEQ ID NO 4
<211> LENGTH: 80
<212> TYPE: DNA
```

```
<213> ORGANISM: Spinacia oleracea

<400> SEQUENCE: 4
attgtacaaa tttcagaaac agttataacc aaattcagat aataaacaga tttccacttc    60
acatatttct tacctcaarc                                                80

<210> SEQ ID NO 5
<211> LENGTH: 83
<212> TYPE: DNA
<213> ORGANISM: Spinacia oleracea

<400> SEQUENCE: 5
cataaacatt ccgtatgagt agtactctat ttgtctcaaa aagaaaattg aaaattgccc    60
tagtcgaaat tttatctgca cta                                            83

<210> SEQ ID NO 6
<211> LENGTH: 82
<212> TYPE: DNA
<213> ORGANISM: Spinacia oleracea

<400> SEQUENCE: 6
cataaacatt ccgtatgagt agtactctat ttgtctcaaa aagaaaattg aaaattgcct    60
agtcgaaatt ttatctgcac ta                                             82

<210> SEQ ID NO 7
<211> LENGTH: 49
<212> TYPE: DNA
<213> ORGANISM: Spinacia oleracea

<400> SEQUENCE: 7
gatgctcagc cgctcaccag tatttggttt tcatgagcca aaaactgga                49

<210> SEQ ID NO 8
<211> LENGTH: 49
<212> TYPE: DNA
<213> ORGANISM: Spinacia oleracea

<400> SEQUENCE: 8
gatgctcagc cgctcaccag tatctggttt tcatgagcca aaaactgga                49
```